United States Patent
Gray

(10) Patent No.: US 11,751,802 B2
(45) Date of Patent: Sep. 12, 2023

(54) POSTURE MEASURING DEVICE

(71) Applicant: Florida A & M University, Tallahassee, FL (US)

(72) Inventor: Kurt William Gray, Tallahassee, FL (US)

(*) Notice: Subject to any disclaimer, the term of this patent is extended or adjusted under 35 U.S.C. 154(b) by 415 days.

(21) Appl. No.: 16/879,072

(22) Filed: May 20, 2020

(65) Prior Publication Data
US 2020/0367806 A1 Nov. 26, 2020

Related U.S. Application Data

(60) Provisional application No. 62/850,091, filed on May 20, 2019.

(51) Int. Cl.
*A61B 5/00* (2006.01)
*A61B 90/00* (2016.01)

(52) U.S. Cl.
CPC ............ *A61B 5/4561* (2013.01); *A61B 90/06* (2016.02); *A61B 2090/061* (2016.02)

(58) Field of Classification Search
CPC ..... A61B 5/107; A61B 5/1077; A61B 5/1116; A61B 5/4561; A61B 90/06; A61B 90/061
See application file for complete search history.

(56) References Cited

U.S. PATENT DOCUMENTS

| | | | | |
|---|---|---|---|---|
| 2,052,099 A * | 8/1936 | Lytton | ...................... | A41H 1/04 33/8 |
| 2,053,810 A * | 9/1936 | Bisel | ........................ | A41H 1/04 33/2 R |
| 2,818,648 A * | 1/1958 | Jochheim | .................. | A41H 1/04 33/8 |
| 3,955,285 A * | 5/1976 | Moeckl | .................. | G01B 5/207 33/515 |
| 5,101,835 A * | 4/1992 | DelRe | .................. | A61B 5/1077 33/555 |
| 6,196,981 B1 * | 3/2001 | Gustafson | ............ | A61B 5/1075 600/587 |
| 6,969,360 B1 * | 11/2005 | Pai | ........................ | A61B 5/103 600/595 |

OTHER PUBLICATIONS

Grimmer K., "Measurement of Cervical Excursion Angles in a Treatment Setting", Physiotherapy, Jul. 1993, vol. 79: pp. 451-456.

(Continued)

*Primary Examiner* — Larry E Waggle, Jr.
(74) *Attorney, Agent, or Firm* — Thomas | Horstemeyer, LLP; Stephanie Davy-Jow

(57) ABSTRACT

Provided are embodiments of a posture measuring device for determining the forward head posture of a patient. Forward head posture (FHP) is the anterior positioning of the cervical spine that is caused by sleeping with the head elevated, extended use of computers and cellphones, lack of developed back muscle strength and lack of nutrients such as calcium. This deformation is associated with headaches, neck pain, thoracic spine pain and symptoms of pain, parastesia or numbness in the upper extremities. The device of the disclosure provides a numerical measurement of the displacement of the skull from the vertical as defined by a datum between the two most posterior points of a patient's spine.

5 Claims, 8 Drawing Sheets

(56) References Cited

OTHER PUBLICATIONS

Hansraj K., "Assessment of Stresses in the Cervical Spine Caused by Posture and Position of the Head" (2014) Surgical Technology. International. 25: pp. 277-279.

Hickey et al., "Reliability of the Cervical Range of Motion (CROM) Device and Plumb-Line Techniques in Measuring Resting Head Posture (RHP)", The Journal of Manual & Manipulative Therapy, vol. 8 No. 1 (2000), pp. 10-17.

Lau et al., "Relationships between sagittal postures of thoracic and cervical spine, presence of neck pain, neck pain severity and disability", Manual Therapy 15 (2010) pp. 457-462.

Mani et al., "Quantitative measurements of forward head posture in a clinical settings: a technical feasibility study", European Journal of Physiotherapy, (2017) vol. 19, No. 3, pp. 119-123.

Ruivo et al., "Effects of a Resistance and Stretching Training Program on Forward Head and Protracted Shoulder Posture in Adolescents", Journal of Manipulative and Physiological Therapeutics, Jan. 2017 vol. 40, pp. 1-10.

Satpute et al., "Quadriceps Femoris Strength Training: effect of Neuromuscular Electrical Stimulation Vs Isometric Exercise in Osteoarthritis of Knee", Indian Journal of Physiotherapy & Occupational Therapy, Jul.-Sep. 2015, vol. 9, No. 3., pp. 1-287.

Yip et al., "The relationship between head posture and severity and disability of patients with neck pain", (2008) Manual Therapy 13, pp. 148-154.

American Physical Therapy Association, 2009, Physical Therapist productivity summary report., pp. 1-4.

Griegel-Morris et al., "Incidence of Common Postural Abnormalities in the Cervical, Shoulder, and Thoracic Regions and Their Association with Pain in Two Age Groups of Healthy Subjects", Physical Therapy/vol. 72, No. 6, Jun. 1992, pp. 425-431.

Garrett et al., "Reliability of Measuring Forward Head Posture in a Clinical Setting", Mar. 1993, J. Orthopaedic Sports Physical Therapy vol. 17, No. 3, pp. 155-160.

* cited by examiner

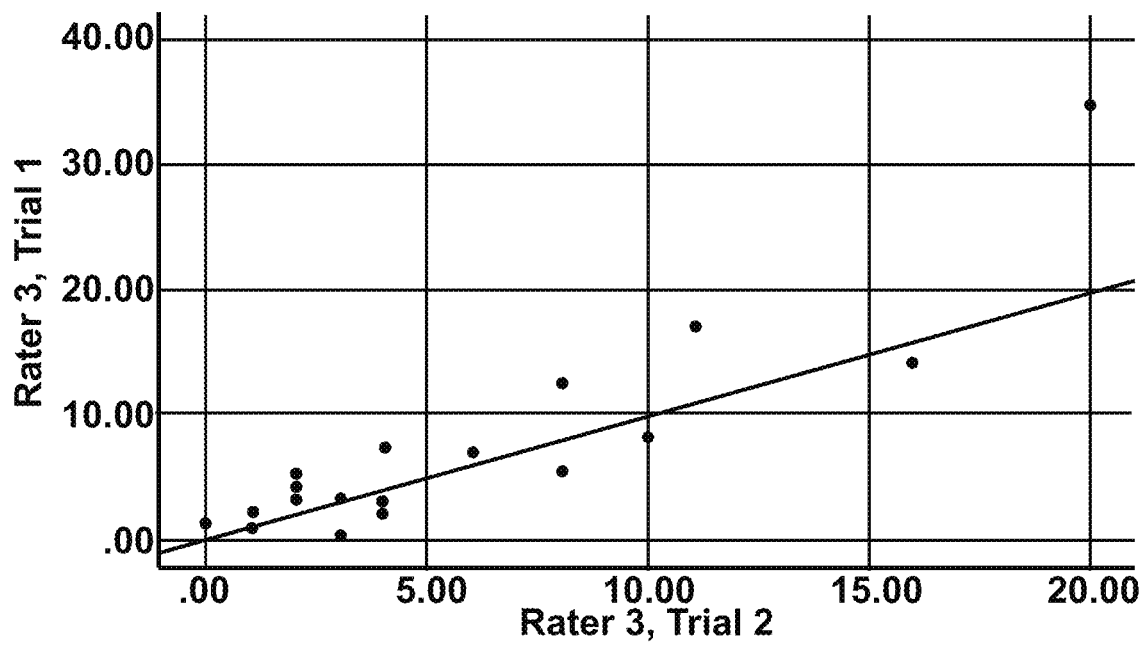
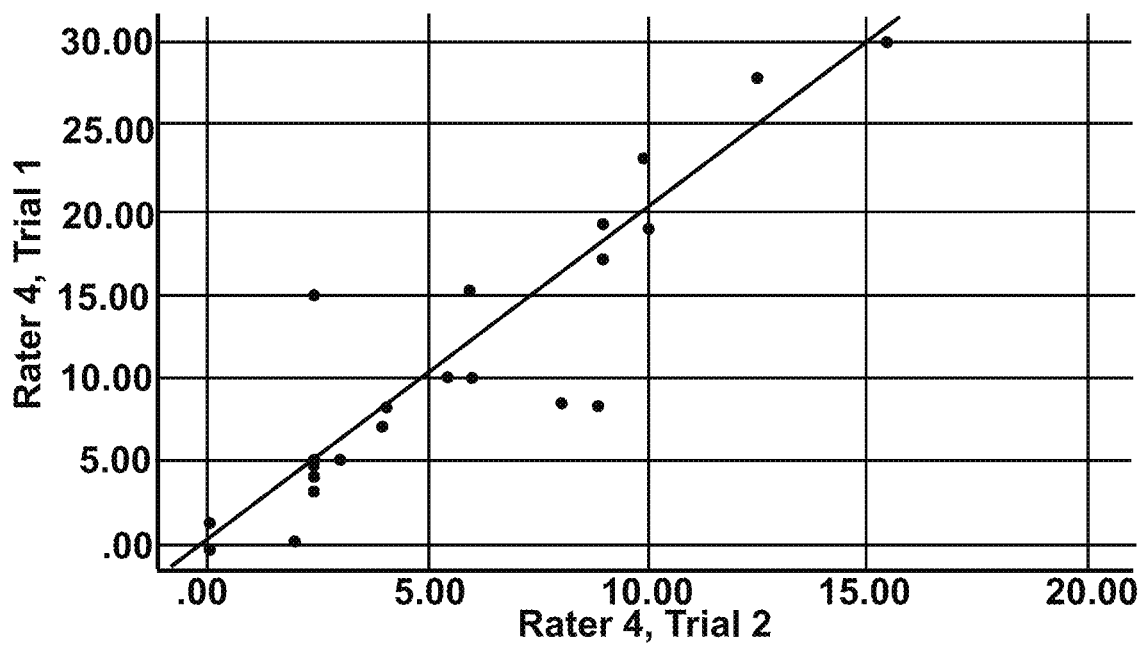
*Fig. 7-Cont'd*

POSTURE MEASURING DEVICE

CROSS-REFERENCE TO RELATED APPLICATIONS

This application claims priority to U.S. Provisional Patent Application Ser. No. 62/850,091 entitled "POSTURE MEASURING DEVICE" filed on May 20, 2019, the entirety of which is hereby incorporated by reference.

TECHNICAL FIELD

The present disclosure is generally related to a posture measuring device. The present disclosure is also generally related to methods of use of the posture measuring device.

BACKGROUND

The practice of outpatient physical therapy is fast-paced. An average therapist often treats as many as 55 patient visits weekly ((2009) *Physical Therapist productivity summary report*). In this setting, cervical spine pain with accompanying forward head posture (FHP) is a common diagnosis, resulting in significant financial and quality of life impacts (Mani et al., (2017) *Eur. J. Physiotherapy* 19: 119-123).

Often a patient referred with non-traumatic cervical spine pain presents without objective or radiographic testing to support and further define the diagnosis (Yip et al., (2008) *Manual Therapy* 13: 148-154). One of the most common findings in the examination of a patient with cervical spine pain is FHP (Ruivo et al., (2017) *J. Manipulative Physiol. Therapeutics* 40: 1-10), described by Yip et al., ((2008) *Manual Therapy* 13: 148-154) as the postural position where the center of gravity of the head is moved anterior to the vertical plumb line that extends from the tragus of the ear through the acromion and proceeding through the body to the floor when observed from the sagittal plane (FIG. 5). FHP has been shown to increase the forces on the neck leading to early degeneration of the cervical structures (Hansraj K. (2014) *Surg. Technol. Internat.* 25: 277-279).

There are multiple ways to measure forward head posture. The tools considered to be most appropriate for use in the clinical setting include the Linear Excursion Measurement Device (LMED) developed in 1993 and the Cervical Range of Motion (CROM) device (Grimmer K. (1993) *Physiotherapy* 79: 451-456). Both of these tools are proven reliable in the clinical setting (Hickey et al., (2000) *J. Manual Manipulative Therapy* 8: 10-17). Other tools, such as flexible rulers, radiographs, computer tomography, and digital photography can accurately measure FHP, but they are not frequently used in the clinical setting (Satpute et al., (2015) Indian *J. Physiotherapy Occupational Therapy* 9: 37). However, even though subjective descriptions are considered inconsistent and inaccurate they remain the most common way that FHP is documented in the clinic (Garrett et al., (1993) *J. Orthopaedic Sports Physical Therapy* 17: 155; Griegel-Morris et al., (1992) *Physical Therapy* 72: 425-431; Lau et al., (2010) *J. Rehabilitation Res. Develop.* 47: 911)

SUMMARY

One aspect of the disclosure, therefore, encompasses embodiments of posture measuring device 1 comprising a first elongated member 10, a second elongated member 11 rigidly attached at a right-angle to the first elongated member 10, and a moveable third elongated member 12 slidably disposed on the first elongated member 10, wherein the first elongated member 10 has an inner edge (16) facing an inner edge (17) of the second elongated member 11, and wherein the moveable third elongated member 12 having a proximal end (18) can extend beyond the first elongated member 10 in the direction of, and parallel to, the second elongated member 11.

In some embodiments of this aspect of the disclosure the posture measuring device can further comprising a channel traversing the first elongated member and configured for slidably receiving the moveable third elongated member in a direction parallel to the second elongated member.

In some embodiments of this aspect of the disclosure the posture measuring device can further comprise at least one retaining shelf disposed on the first elongated member and configured for slidably receiving the moveable third elongated member in a direction parallel to the second elongated member.

In some embodiments of this aspect of the disclosure the posture measuring device can further comprise a support mounting attached to the posture measuring device.

In some embodiments of this aspect of the disclosure the support mounting can be a floor stand or a support mounting is attached to a wall.

Another aspect of the disclosure encompasses embodiments of a method of measuring forward head posture of a subject, the method comprising contacting a subject with a posture measuring device 1 comprising a first elongated member 10, a second elongated member 11 rigidly attached at a right-angle to the first elongated member 10, and a moveable third elongated member 12 slidably disposed on the first elongated member 10, wherein the first elongated member 10 has an inner edge (16) facing an inner edge (17) of the second elongated member 11, and wherein the moveable third elongated member 12 having a proximal end (18) can extend beyond the first elongated member 10 in the direction of, and parallel to, the second elongated member 11, by placing the inner edge (16) of the first elongated member (10) of the postural measuring device (1) along the posterior aspect of the spine of a subject and making contact with the patient with the surface apex of the thoracic kyphosis cephalically and the median sacral crest caudally; moving the posture measuring device 1 caudally until the inner surface (17) second elongated member (11) meets the top of the head; sliding the moveable third elongated member (12) until the proximal end (18) thereof it contacts the posterior aspect of the head of the subject; and reading the length of protrusion of the moveable third elongated member (12) beyond the inner surface (16) of the first elongated member (10) from a scale (19) on the moveable third elongated member (12), thereby generating a measurement of the forward head posture of the patient.

BRIEF DESCRIPTION OF THE DRAWINGS

Further aspects of the present disclosure will be more readily appreciated upon review of the detailed description of its various embodiments, described below, when taken in conjunction with the accompanying drawings.

DETAILED DESCRIPTION

Figure 1:
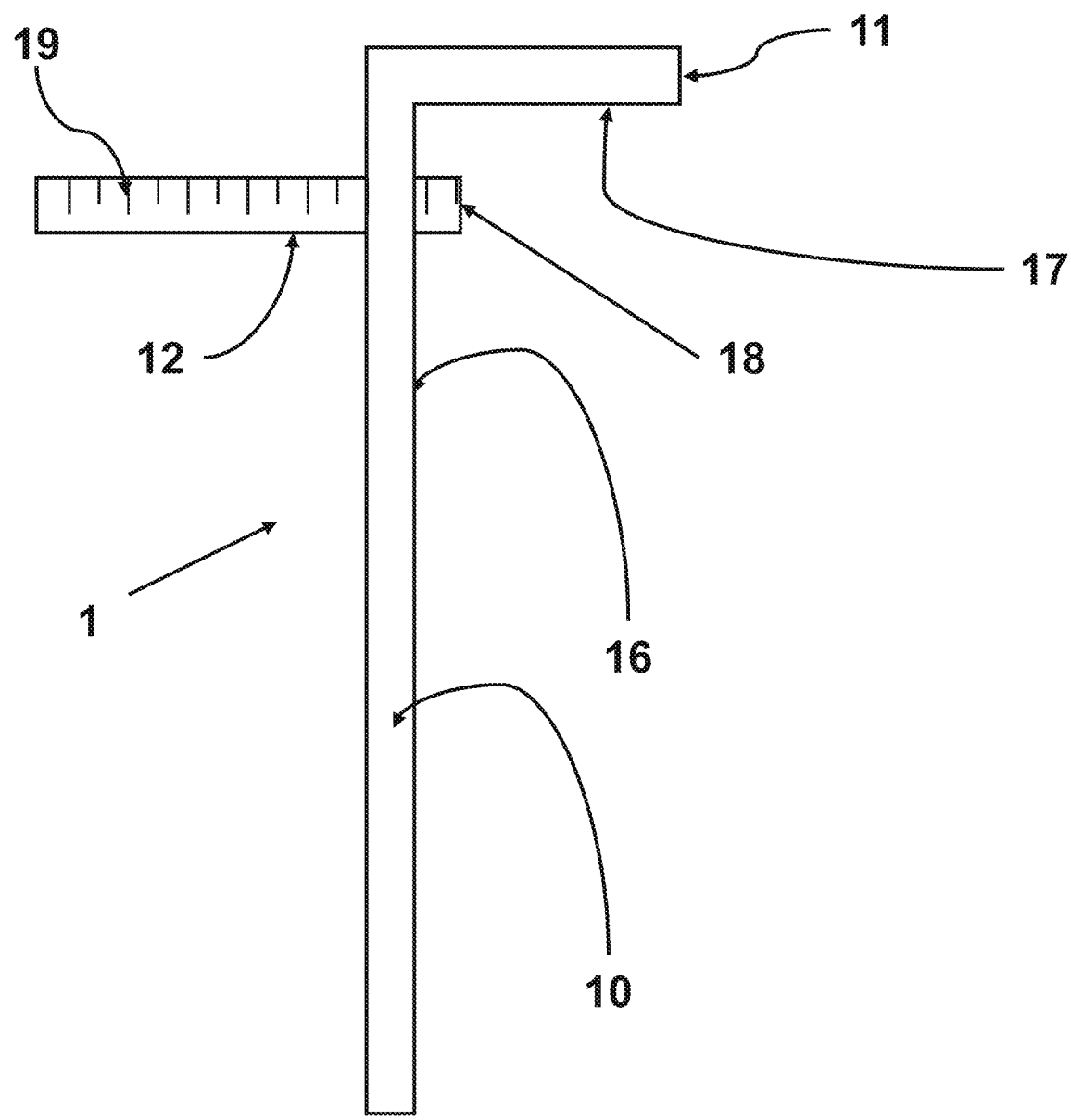
FIG. 1 illustrates a side-view of a posture measuring device (1) according to the disclosure.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

DISCUSSION

The present disclosure encompasses embodiments of a posture measuring device for determining the forward head posture of a patient. The human neck has evolved to remain essentially vertical, maintaining the weight of the skull in a perfect line from the top of the head straight down through the body to the feet. Forward head posture (FHP) is the anterior positioning of the cervical spine that is caused by several factors including sleeping with the head elevated too high, extended use of computers and cellphones, lack of developed back muscle strength and lack of nutrients such as calcium. Besides issues of appearance, this deformation is associated with negative effects including, but not limited to, headaches, neck pain, thoracic spine pain and symptoms of pain, parastesia or numbness in the upper extremities. The device of the disclosure provides a numerical measurement of the displacement of the skull from the vertical as defined by a datum between the two most posterior points of a patient's spine.

Embodiments of the posture measuring device (1) of the disclosure, therefore, comprise a first elongated member (10), most advantageously rigidly attached or disposed at right-angles to a second elongated member (11). Each of the first (10) and the second (11) elongated members has an inside edge (16 and 17, respectively), the two inside edges facing one another. The device of the disclosure can further comprise a third elongated member (12) moveably engaging with the first elongated member (10) having a proximal end (18) and moveable in a direction substantially parallel to the second elongated member (11). The moveable third elongated member (12) can include a scale (19), graduated, for example, in inches or metric units that provides a measurement of the proximal end (18) from the facing inner edge (16) of the first elongated member (10).

Figure 5:
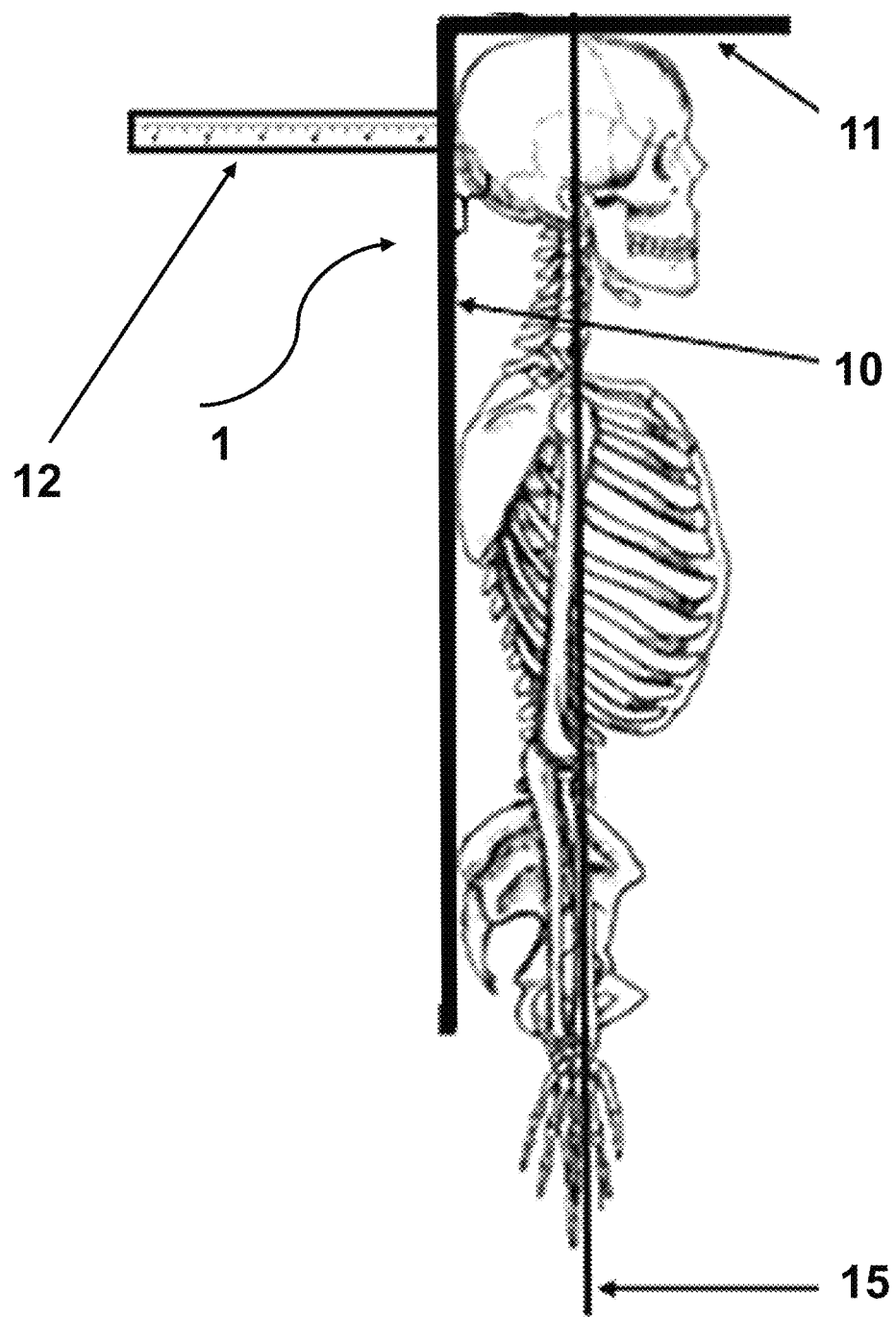
FIG. 5 illustrates a side-view of a posture measuring device (1) according to the disclosure in position relative to a human skeleton.
Figure 6:
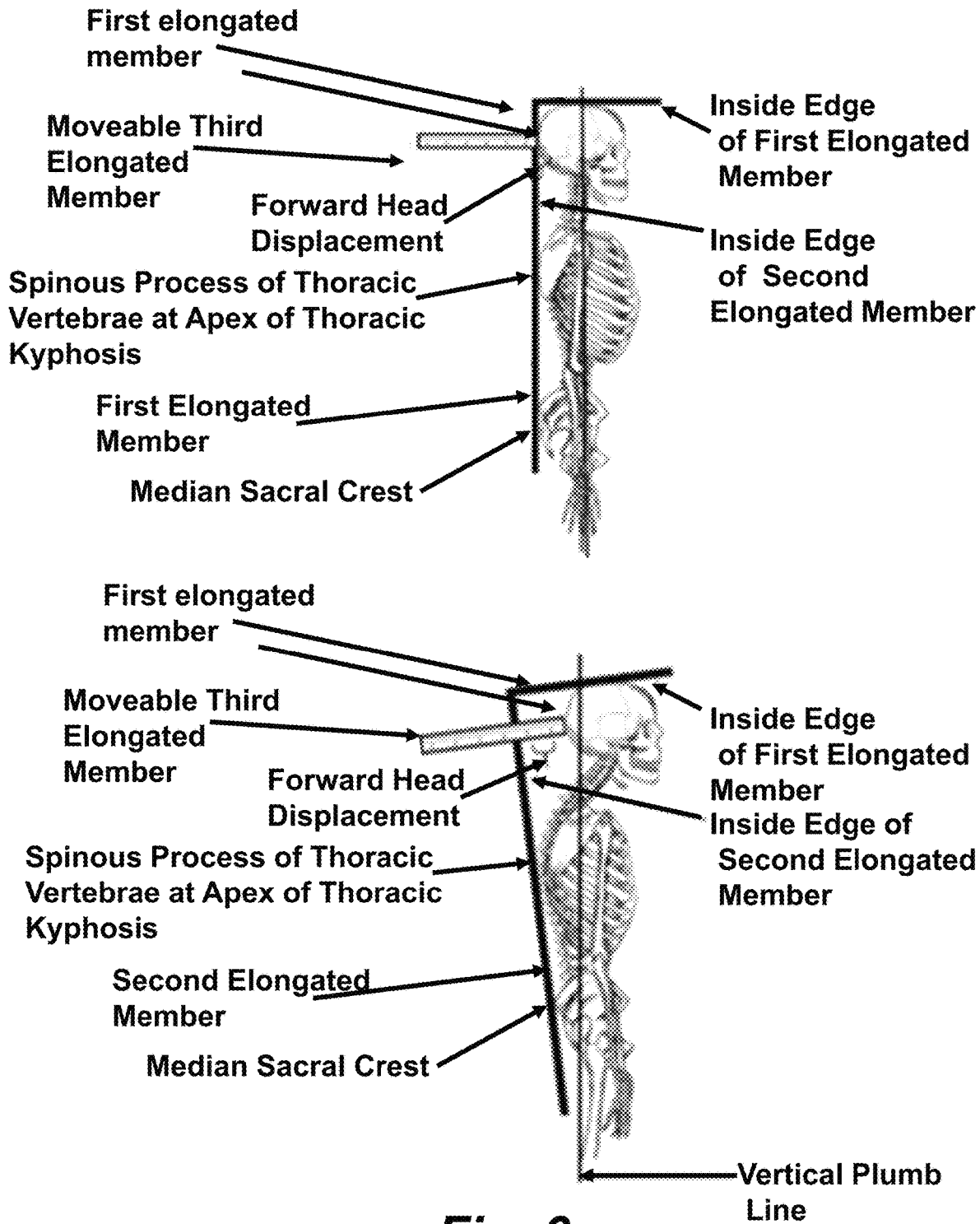
FIG. 6 illustrates a pair of side-views of a posture measuring device (1) according to the disclosure in position relative to a human skeleton.
Figure 7:
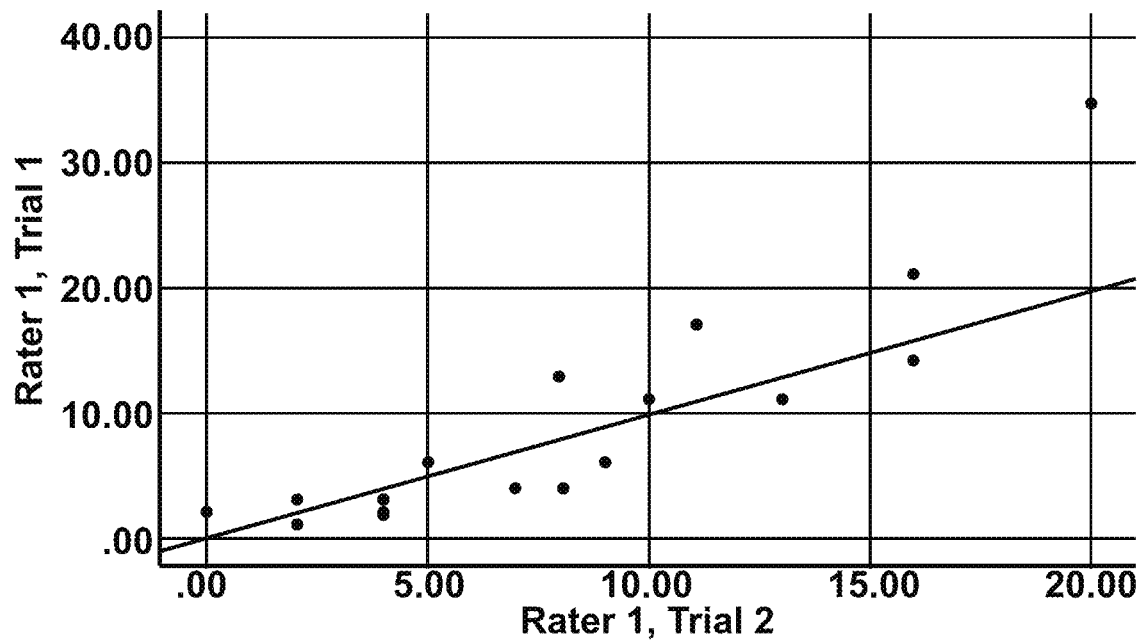
FIG. 7 illustrates graphs of the data used for Table 1.
Figure 7:
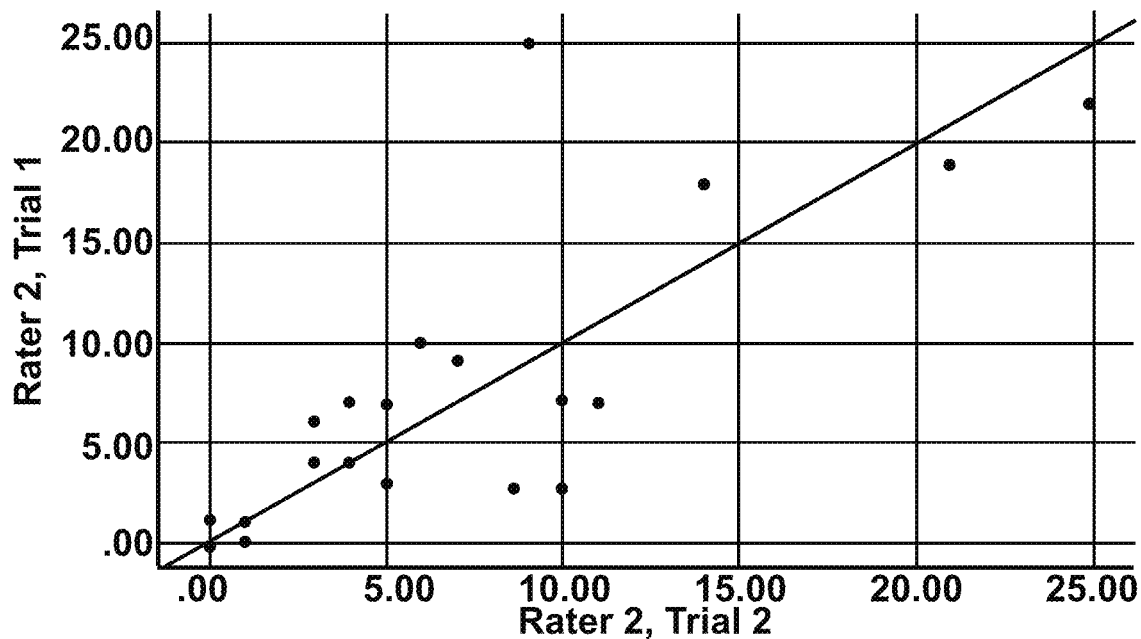

As schematically shown in FIGS. 5 and 6, when in use, the inside edge (16) of the first elongated member (10) can be placed against the spine of the patient, the first elongated member (10) being of sufficient length that it can be placed against at least two dorsal points of the spine curvature. The inner surface (17) of the second elongated member (11) is placed in contact with the uppermost point of the skull when the patient is standing in a relaxed vertical posture. The moveable third elongated member (12) is extended to contact the base of the skull, providing a measurement from the scale (19) of the distance from the inside edge (16) of the first elongated member (10) to the base of the skull, the measurement defining the degree of displacement of the skull from the vertical axis of the spine.

In embodiments of the device, the first (10) and second (10) elongated members may be manufactured as a single contiguous unit with the two members rigidly configured at right-angles by such as by plastic molding. In some embodiments, the first (10) and second (10) elongated members may be manufactured as separate items that are rigidly attached to each other at the desired angle, most preferably at right-angles, by using such as, but not limited to, an adhesive, a nut and bolt assembly, or other means well known in the art. In some embodiments the first (10) and second (10) elongated members may be connected by a means that allows adjustment of the angle between them. In some embodiments the postural measuring device (1) of the disclosure may be held against the patient by hand, or may be supported by a floor-stand, for example.

Referring now to FIG. 1, shown is a side-view of an embodiment of a T-square-shaped postural measuring device (1) comprising a first elongated member (10) that is secured or contiguous with, and at a right angle to, a second elongated member (11). Below the second elongated member (11) is situated a moveable third elongated member (12) crossing the first elongated member (10) at a right angle and capable of moving such that the first elongated member (10) can be variably positioned along the moveable third elongated member (12). The moveable third elongated member (12) protrudes from the first elongated member (10) parallel to the second elongated member (11).

In some embodiments of the postural measuring device (1) of the disclosure the moveable third elongated member can have a distance scale that allows for a determination of the extent of the protrusion of the moveable third elongated member (12) from the first elongated member (10) in the direction of the second.

In some embodiments of the postural measuring device (1) of the disclosure the moveable third elongated member (12) can be slidably disposed on the first elongated member (10) such that it can be positioned at a required distance from the second elongated member (11). For example, but not intended to be limiting, an advantageous distance between the facing inner surface (17) second elongated member (11) and the moveable third elongated member (12) can be about 7.5 cm, necessary to maintain a consistent placement on the posterior aspect of the head, as shown in FIG. 5.

Figure 2:
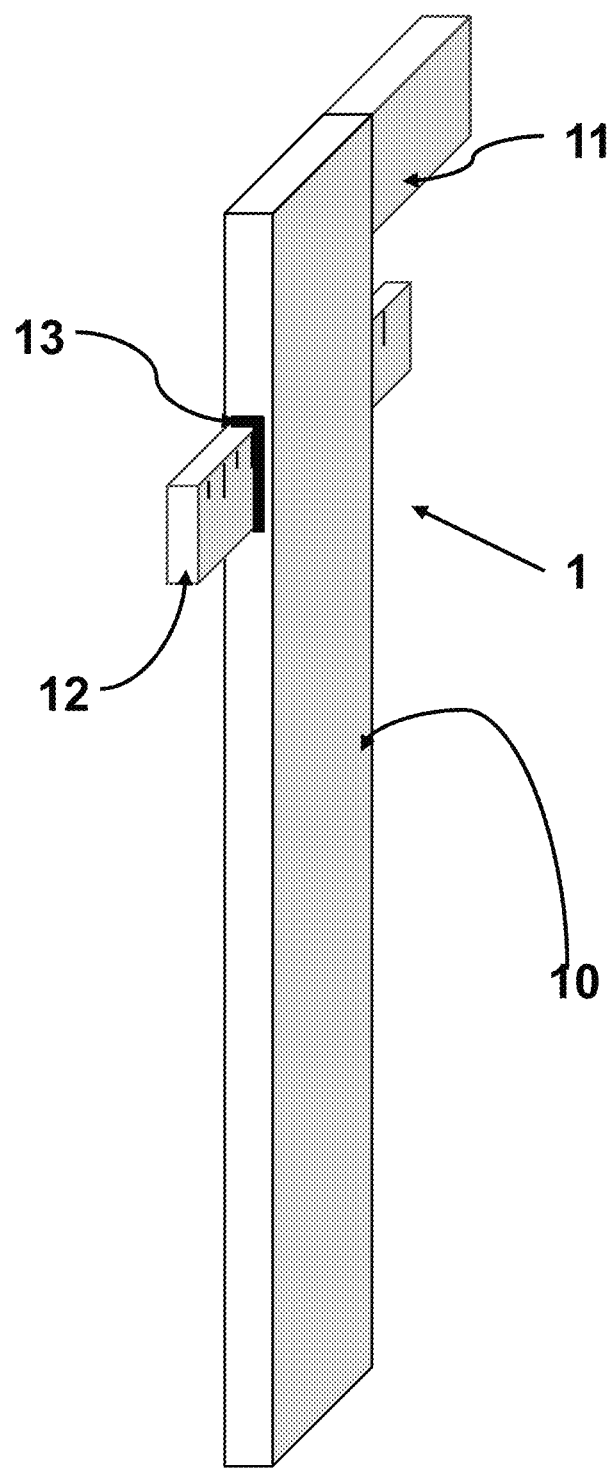
FIG. 2 illustrates a perspective view of a posture measuring device (1) according to the disclosure.

Referring now to FIG. 2, shown is a perspective view of an embodiment of the postural measuring device (1) of the disclosure wherein the moveable third elongated member (12) is moveably disposed within a rectangular channel (13) traversing the first elongated member (10) that allows the moveable third elongated member (12) to be variable positioned relative to, and extending from, the first elongated member (10) and parallel to the second elongated member (11).

Figure 3:
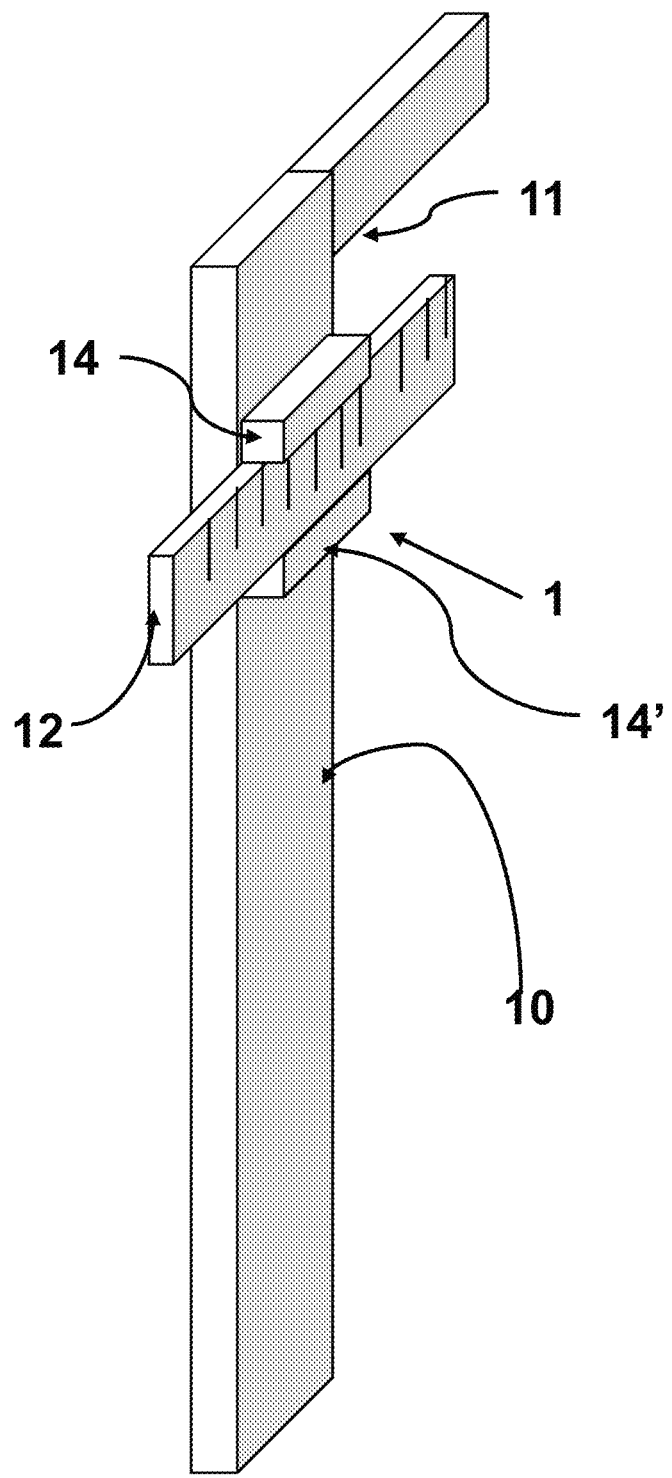
FIG. 3 illustrates a perspective view of a posture measuring device (1) according to the disclosure.

Referring now to FIG. 3, shown is a perspective view of an embodiment of the postural measuring device (1) of the disclosure wherein the moveable third elongated member (12) is moveably disposed within a pair of supports (14, 14') that allows the moveable third elongated member (12) to be variably positioned relative to, and extending beyond the first elongated member (10) and parallel to the second elongated member (11).

Figure 4:
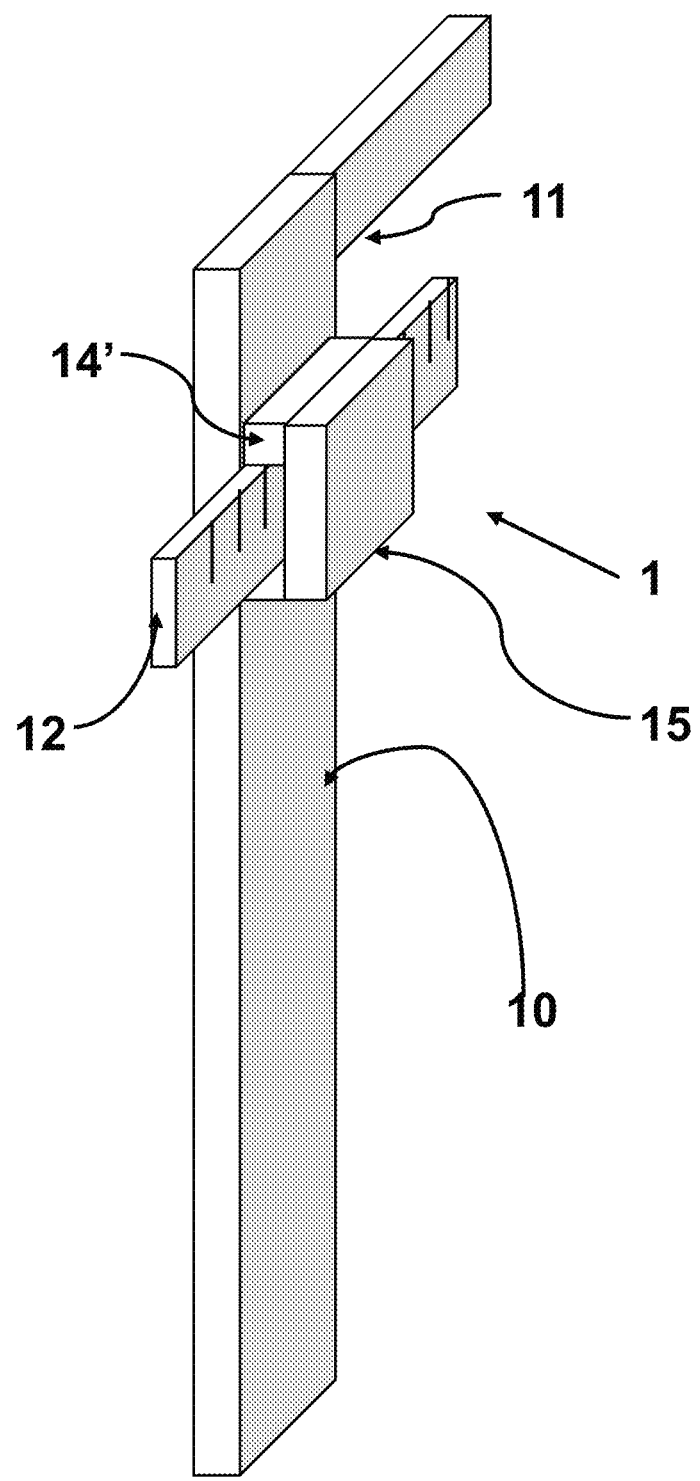
FIG. 4 illustrates a perspective view of a posture measuring device (1) according to the disclosure.

Referring now to FIG. 4, shown is a perspective view of an embodiment of the postural measuring device (1) of the disclosure wherein the moveable third elongated member (12) is moveably disposed within a pair of supports (14) that allows the moveable third elongated member (12) to be variably positioned relative to, and extending beyond the first elongated member (10) and parallel to the second elongated member (11), and a facia panel (15) to moveably contain the moveable third elongated member (12) against the first elongated member (10).

One of skill in the art will recognize that the postural measuring device (1) of the disclosure may further comprise a means to secure the moveable third elongated member (12) in a fixed position relative to the first elongated member (10). For example such means can be a spring to provide friction of such strength as to hold the moveable third elongated member (12) without undesirable or inadvertent shifting of the member (12) relative to the first elongated member (10).

Postural Measuring Device (1) Placement and Measurement Procedure

Referring now to FIG. 5, a method of use of the postural measuring device (1) of the disclosure can comprise placing the first elongated member (10) of the postural measuring device (1) of the disclosure along the posterior aspect of the spine of a subject making contact with the apex of the thoracic kyphosis cephalically and the median sacral crest caudally. The postural measuring device (1) is then is moved caudally until the second elongated member (11) meets the top of the head.

To ensure the participant has acquired the necessary proper position, the participant can be directed to stand as erect as possible and then directed to relax into a normal posture. With the participant standing in a normal posture, the moveable third elongated member (12) is slid anteriorly until it contacts the posterior aspect of the head. A measurement can then be obtained by reading the length of protrusion of the moveable third elongated member (12) beyond the first elongated member (10) from a scale (19) on the moveable third elongated member (12).

The results as shown in the examples confirm the intra-rater and inter-rater reliability of the postural measuring device (1) of the disclosure as found in a pilot study. The time required to obtain a measurement of FHP using the postural measuring device (1) was estimated to take less than 60 seconds. The postural measuring device (1) of the disclosure demonstrates an advantage in delivering reliable measurements that fit within the fast pace of an outpatient physical therapy practice.

One aspect of the disclosure, therefore, encompasses embodiments of posture measuring device 1 comprising a first elongated member 10, a second elongated member 11 rigidly attached at a right-angle to the first elongated member 10, and a moveable third elongated member 12 slidably disposed on the first elongated member 10, wherein the first elongated member 10 has an inner edge (16) facing an inner edge (17) of the second elongated member 11, and wherein the moveable third elongated member 12 having a proximal end (18) can extend beyond the first elongated member 10 in the direction of, and parallel to, the second elongated member 11.

In some embodiments of this aspect of the disclosure the posture measuring device can further comprising a channel traversing the first elongated member and configured for slidably receiving the moveable third elongated member in a direction parallel to the second elongated member.

In some embodiments of this aspect of the disclosure the posture measuring device can further comprise at least one retaining shelf disposed on the first elongated member and configured for slidably receiving the moveable third elongated member in a direction parallel to the second elongated member.

In some embodiments of this aspect of the disclosure the posture measuring device can further comprise a support mounting attached to the posture measuring device.

In some embodiments of this aspect of the disclosure the support mounting can be a floor stand or a support mounting is attached to a wall.

Another aspect of the disclosure encompasses embodiments of a method of measuring forward head posture of a subject, the method comprising contacting a subject with a posture measuring device 1 comprising a first elongated member 10, a second elongated member 11 rigidly attached at a right-angle to the first elongated member 10, and a moveable third elongated member 12 slidably disposed on the first elongated member 10, wherein the first elongated member 10 has an inner edge (16) facing an inner edge (17) of the second elongated member 11, and wherein the moveable third elongated member 12 having a proximal end (18) can extend beyond the first elongated member 10 in the direction of, and parallel to, the second elongated member 11, by placing the inner edge (16) of the first elongated member (10) of the postural measuring device (1) along the posterior aspect of the spine of a subject and making contact with the patient with the surface apex of the thoracic kyphosis cephalically and the median sacral crest caudally; moving the posture measuring device 1 caudally until the inner surface (17) second elongated member (11) meets the top of the head; sliding the moveable third elongated member (12) until the proximal end (18) thereof it contacts the posterior aspect of the head of the subject; and reading the length of protrusion of the moveable third elongated member (12) beyond the inner surface (16) of the first elongated member (10) from a scale (19) on the moveable third elongated member (12), thereby generating a measurement of the forward head posture of the patient.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

Methods:

A sample of 32 healthy volunteers were used. Subjects reporting a history of a neck injury requiring medical attention, or autoimmune disease that could affect joint integrity were excluded. Additionally, subjects currently taking pain medication or reporting headache, pain in the neck, upper back, shoulder or arm were excluded. The remaining 23 subjects were measured using the PMD by a panel of four raters composed of two experienced physical therapists and two less experienced students on two separate occasions.

Example 2

Each of four raters measured each participant. To observe the effect of professional experience, raters A and B were 2$^{nd}$ year physical therapy students and raters C and D were manned by physical therapists.

After each measurement by each rater, the participant was directed to the next rater. Following measurement by all raters, the subject was directed to return to the end of the line to await a repeated measurement by all raters.

The second measurement of each participant was obtained using the same procedure in the same order as the first measurement by each rater.

The mean measurements by each rater, shown in Table 1, range from 6.13 (SD 8.35) to 19.61 (SD 13.86).

TABLE 1

Intraclass Correlation Coefficient and Pearson Correlation Scores

| Rater 1: | $\alpha = 0.905$ | $P = 1.679 \times 10^{-7}$ |
| Rater 2: | $\alpha = 0.859$ | $P = 9.6 \times 10^{-5}$ |
| Rater 3: | $\alpha = 0.872$ | $P = 1.0 \times 10^{-6}$ |
| Rater 4: | $\alpha = 0.969$ | $P = 3.6852 \times 10^{-9}$ |

The results of the correlations show each rater with a high intra-rater correlation. However, the bivariate inter-rater correlation does not consistently indicates significant measurement associations.

The results support a high degree of reliability between the eight measurements. The average measure ICC was 0.822 with a 95% confidence interval from 0.687 to 0.914 (F (22, 161)=5.624, p<0.000).

TABLE 2

Intraclass Correlation Coefficient

| | Intraclass Correlation | 95% C.I. Lower | 95% C.I. Upper | F Test with True Value 0 Value | Df1 | Df2 | Sig |
|---|---|---|---|---|---|---|---|
| Single Measures | .366 | .215 | .569 | 5.624 | 22 | 161 | .000 |
| Average Measures | .822 | .687 | .914 | 5.624 | 22 | 161 | .000 |

One-way random effects model where people effects are random

This finding suggests indicates significant measurement correlation among the raters. The data were also analyzed using Cronbach's alpha, confirming the ICC findings of strong correlation among the eight raters ($\alpha=0.87$).

TABLE 3

Cronbach's Alpha Analysis

| Cronbach's Alpha | N of Items |
|---|---|
| .866 | 8 |

Although the Pearson's rho, ICC, and Cronbach's alpha each reveal high correlations among the measures and raters, high correlation does not imply high agreement. The Bland-Altman analysis is an alternate way to capture systematic or proportional bias. The analysis investigates systematic differences between measurements and identifies possible outliers. The Bland-Altman regression results are presented in Table 4.

| | | β | S.E. | T | p value |
|---|---|---|---|---|---|
| Rater A | (Constant) | 2.005 | 3.471 | .578 | .570 |
| | Mean | .103 | .162 | .637 | .531 |
| Rater B | (Constant) | −.705 | 1.087 | −.648 | .524 |
| | Mean | .257 | .097 | 2.659 | .015 |
| Rater C | (Constant) | −.746 | 1.372 | −.544 | .592 |
| | Mean | .319 | .104 | 3.066 | .006 |
| Rater D | (Constant) | −.611 | 3.348 | −.182 | .857 |
| | Mean | .163 | .158 | 1.030 | .315 |

The results show that that for Rater A and Rater D measurements did not reflect any proportional bias. Thus, the results for these two raters are unbiased. However, the results for Rater B and Rater C reflect a degree of bias. To address this, the data was graphed using a Bland-Altman scatter plot. A review of the plots reveals that the majority (96%) of scores are within the expected range for both Rater B and Rater C.

What I claim:

1. A posture measuring device (1) comprising a first elongated member (10), a second elongated member (11) rigidly attached at a right-angle to the first elongated member (10), and a moveable third elongated member (12) slidably disposed on the first elongated member (10), wherein the first elongated member (10) has an inner edge (16) facing an inner edge (17) of the second elongated member (11), and wherein the moveable third elongated member (12) having a proximal end (18) can extend beyond the first elongated member (10) in a direction of, and parallel to, the second elongated member (11), and wherein the device (1) can be raised or lowered, and wherein a distance between the second elongated member (11) and the moveable third elongated member (12) is fixed, and wherein the device is both handheld and freely movable by a user while measuring a subject.

2. The posture measuring device (1) of claim 1, further comprising a channel traversing the first elongated member (11) and configured for slidably receiving the moveable third elongated member (12) in a direction parallel to the second elongated member (11).

3. The posture measuring device (1) of claim 1, further comprising at least one retaining shelf (14, 14') disposed on the first elongated member (10) and configured for slidably receiving the moveable third elongated member (12) in a direction parallel to the second elongated member (11).

4. The posture measuring device (1) of claim 1, wherein the device (1) is configured such that a user can move the device such that:

the inner edge (16) of the first elongated member (10) is in contact with a posterior aspect of a spine of the subject at both a surface apex of a thoracic kyphosis cephalically and a median sacral crest caudally, the inner edge (17) of the second elongated member (11) is in contact with a top of a head of the subject, and the proximal end (18) of the moveable third elongated member (12) is in contact with a posterior aspect of the head of the subject.

5. A method of measuring forward head posture of a subject, the method comprising contacting a subject with a posture measuring device (1) comprising a first elongated member (10), a second elongated member (11) rigidly attached at a right-angle to the first elongated member (10), and a moveable third elongated member (12) slidably disposed on the first elongated member (10), wherein the first elongated member (10) has an inner edge (16) facing an inner edge (17) of the second elongated member (11), and wherein the moveable third elongated member (12) having a proximal end (18) can extend beyond the first elongated member (10) in a direction of, and parallel to, the second elongated member (11), by placing the inner edge (16) of the first elongated member (10) of the posture measuring device (1) along a posterior aspect of a spine of the subject and making contact with the subject with a surface apex of a thoracic kyphosis cephalically and a median sacral crest caudally; moving the posture measuring device (1) caudally until the inner edge (17) of the second elongated member (11) meets the top of a head of the subject; sliding the moveable third elongated member (12) until the proximal end (18) thereof contacts a posterior aspect of the head of the subject; and reading a length of protrusion of the moveable third elongated member (12) beyond the inner edge (16) of the first elongated member (10) from a scale (19) on the moveable third elongated member (12), thereby generating a measurement of the forward head posture of the subject.

* * * * *